United States Patent [19]

Gehring et al.

[11] Patent Number: 4,740,232
[45] Date of Patent: * Apr. 26, 1988

[54] SUBSTITUTED 5-AMINO-1-PHENYLPYRAZOLES COMPOSITION CONTAINING THEM AND HERBICIDAL METHOD OF USING THEM

[75] Inventors: Reinhold Gehring; Jörg Stetter, both of Wuppertal; Otto Schallner, Monheim; Ludwig Eue, Leverkusen; Hans-Joachim Santel, Colonge; Robert R. Schmidt, Bergisch-Gladbach, all of Fed. Rep. of Germany

[73] Assignee: Bayer Aktiengesellschaft, Leverkusen, Fed. Rep. of Germany

[*] Notice: The portion of the term of this patent subsequent to Mar. 29, 2005 has been disclaimed.

[21] Appl. No.: 754,048

[22] Filed: Jul. 11, 1985

[30] Foreign Application Priority Data

Jul. 18, 1984 [DE] Fed. Rep. of Germany ....... 3426424

[51] Int. Cl.$^4$ .................... A01N 43/56; C07D 231/14
[52] U.S. Cl. ......................... 71/92; 540/597; 540/598; 540/603; 544/82; 544/130; 544/140; 546/187; 546/211; 548/362; 548/374; 548/377
[58] Field of Search ........................ 548/362, 377, 374; 71/92; 544/82, 130, 140; 546/187, 211; 540/597, 598, 603

[56] References Cited

U.S. PATENT DOCUMENTS 4,459,150 7/1984 Hatton et al. ................. 548/377
4,472,192 9/1984 Eicken et al. ..................... 71/92

FOREIGN PATENT DOCUMENTS 0034945 9/1981 European Pat. Off. ............. 71/92
0138149 4/1985 European Pat. Off. ............. 71/92
8300332 2/1983 PCT Int'l Appl. .................. 71/92
2123420 2/1984 United Kingdom .................. 71/92

Primary Examiner—Henry R. Jiles
Assistant Examiner—Kurt G. Briscoe
Attorney, Agent, or Firm—Sprung Horn Kramer & Woods

[57] ABSTRACT

Herbicidally active 5-amino-1-phenylpyrazoles of the formula

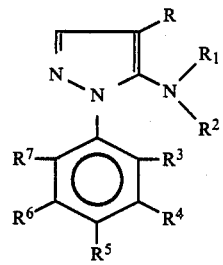

in which
R is CN, or an ester or amido group,
$R^1$ is an organic radical,
$R^2$ is an organic radical, hydrogen or an acyl or thioacyl radical,
$R^3$, $R^4$, $R^5$, $R^6$ and $R^7$ can be hydrogen or various organic radicals but at least one is a haloalkyl, haloalkoxy, haloalkylthio, haloalkylsulphinyl or haloalkylsulphonyl radical, but R is not CN at the same time as $R^5$ is $CF_3$. The compounds

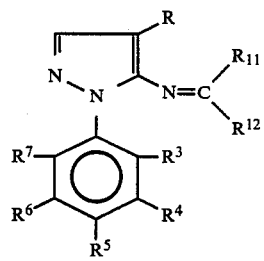

are intermediates therefor and are also herbicidal.

11 Claims, No Drawings

SUBSTITUTED 5-AMINO-1-PHENYLPYRAZOLES COMPOSITION CONTAINING THEM AND HERBICIDAL METHOD OF USING THEM

The invention relates to new substituted 5-amino-1-phenylpyrazoles, several processes for their preparation and their use as herbicides.

It is already known that certain substituted 5-amino-1-phenylpyrazoles, such as, for example, 4-cyano-5-propinamido-1-(2,4,6-trichlorophenyl)- or the corresponding -1-(2,3,4-trichlorophenyl)-pyrazole, have herbicidal properties (compare, for example, DE-OS (German Published Specification) No. 3,226,513).

However, the herbicidal action of these known compounds toward weeds and their tolerance towards important crop plants is not always completely satisfactory in all fields of use.

New substituted 5-amino-1-phenylpyrazoles of the general formula (I)

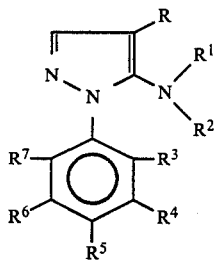

in which

R represents cyano, alkoxycarbonyl, alkenyloxycarbonyl, alkinylcarbonyl, aminocarbonyl, alkylaminocarbonyl, alkenylaminocarbonyl, alkinylaminocarbonyl, dialkylaminocarbonyl, dialkenylaminocarbonyl or dialkinylaminocarbonyl, $R^1$ represents alkyl, alkenyl, alkinyl or cycloalkyl, each of which is optionally substituted, $R^2$ independently of $R^1$ represents the same radicals as $R^1$, and additionally represents hydrogen or a radical

wherein

X represents oxygen or sulphur and $R^8$ represents hydrogen, alkyl, alkenyl, alkinyl, halogenoalkyl, alkoxyalkyl, alkylthioalkyl, optionally substituted cycloalkyl or optionally substituted aryl, or represents alkoxy, alkylthio, optionally substituted aryloxy or optionally substituted arylthio, or represents alkylamino, dialkylamino or optionally substituted arylamino and $R^3$, $R^4$, $R^5$, $R^6$ and $R^7$, which are identical or different, represent hydrogen, halogen, cyano, nitro, alkyl, alkoxy, alkylsulphonyl, alkoxycarbonyl or a radical $-(X')_n-R^9$, wherein $X'$ represents oxygen, sulphur, sulphinyl or sulphonyl, n represents 0 or 1 and $R^9$ represents halogenoalkyl, with the proviso that at least one of the radicals $R^3$, $R^4$, $R^5$, $R^6$ and $R^7$ represents a radical $-(X')_n-R^9$, but R does not represent cyano at the same time as $R^5$ represents trifluoromethyl.

It has furthermore been found that the new substituted 5-amino-1-phenylpyrazoles of the general formula (I) are obtained by a process in which (a) 5-amino-pyrazoles of the formula (II)

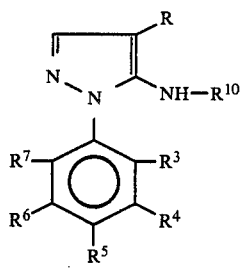

in which

R, $R^3$, $R^4$, $R^5$, $R^6$ and $R^7$ have the abovementioned meaning and $R^{10}$ represents hydrogen or a radical

wherein

X and $R^8$ have the abovementioned meaning, are reacted with alkylating agents of the formula (III)

$$R^1-A \qquad (III)$$

in which $R^1$ has the abovementioned meaning and

A represents an electron-withdrawing leaving group, if appropriate in the presence of a diluent and if appropriate in the presence of an acid-binding agent, and if appropriate in the presence of a catalyst, or in which (b) 5-acylaminopyrazoles of the formula (Ia)

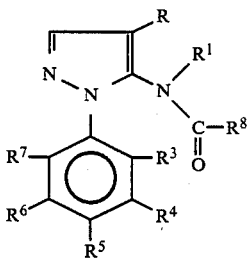

in which

R, $R^1$, $R^3$, $R^4$, $R^5$, $R^6$, $R^7$ and $R^8$ have the abovementioned meaning, are deacylated in the customary manner with acids and bases, if appropriate in the presence of a diluent, or in which (c) azomethines of the formula (IV)

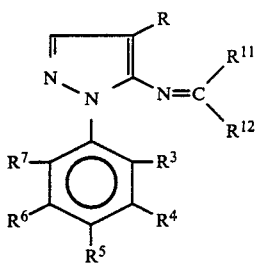

(IV)

in which

R, $R^3$, $R^4$, $R^5$, $R^6$ and $R^7$ have the abovementioned meaning, $R^{11}$ represents alkyl, alkenyl or alkinyl, each of which is optionally substituted, and $R^{12}$ independently of $R^{11}$ represents the same radicals as $R^{11}$, and also represents hydrogen, are reduced with a complex hydride, if appropriate in the presence of a diluent.

Finally, it has been found that the new substituted 5-amino-1-phenylpyrazoles of the formula (I) have herbicidal properties, and in particular also selective herbicidal properties.

Surprisingly, the new substituted 5-amino-1-phenylpyrazoles of the formula (I) have a better herbicidal activity towards harmful plants, coupled with a better tolerance towards important crop plants, than, for example, the compounds 4-cyano-5-propionamido-1-(2,4,6-trichlorophenyl)- and -(2,3,4-trichlorophenyl)-pyrazole, which are known from the prior art and are closely related compounds chemically and from the point of view of their action.

Formula (I) provides a general definition of the new substituted 5-amino-1-phenylpyrazoles. Preferred compounds of the formula (I) are those in which R represents cyano or aminocarbonyl, or represents alkoxycarbonyl, alkenyloxycarbonyl, alkinyloxycarbonyl, alkylaminocarbonyl, alkenylaminocarbonyl, alkinylaminocarbonyl, dialkylaminocarbonyl, dialkenylaminocarbonyl or dialkinylaminocarbonyl, each of which has up to 5 carbon atoms in the individual aliphatic radicals and each of which is sgraight-chain or branched, $R^1$ represents alkyl, alkenyl or alkinyl, each of which has up to 8 carbon atoms and each of which is optionally monosubstituted or polysubstituted by identical or different substituents, possible substituents being: halogen, cyano, nitro, hydroxyl and carboxyl, alkoxy and alkoxycarbonyl, each of which has up to 6 carbon atoms and each of which is straight-chain or branched, and aminocarbonyl which is optionally substituted by alkyl, alkenyl, alkinyl, alkoxy or alkylsulphonyl, it being possible for the nitrogen atom of the aminocarbonyl radical also to be part of a saturated 3-membered to 7-membered heterocyclic radical with up to 2 further heteroatoms, in particular nitrogen, oxygen or sulphur; or represents cycloalkyl which has 3 to 7 carbon atoms and is optionally monosubstituted or polysubstituted by identical or different radicals from the group comprising halogen and straight-chain or branched alkyl with 1 to 4 carbon atoms, $R^2$ independently of $R^1$ represents the same radicals as $R^1$, and also represents hydrogen or a radical

wherein

X represents oxygen or sulphur and $R^8$ represents hydrogen, or represents alkyl, alkenyl, alkinyl, alkoxyalkyl, alkylthioalkyl, alkoxy, alkylthio, alkylamino, dialkylamino or halogenoalkyl, each of which has up to 4 carbon atoms in the individual alkyl parts and each of which is straight-chain or branched, halogenoalkyl having up to 9 identical or different halogen atoms, or represents cycloalkyl which has 3 to 7 carbon atoms and is optionally monosubstituted or polysubstituted by identical or different substituents from the group comprising halogen, lower alkyl and lower halogenoalkyl, or represents phenyl, phenoxy, phenylthio or phenylamino, each of which is optionally monosubstituted or polysubstituted by identical or different substituents, possible substituents of the phenyl being: halogen and alkyl, alkoxy and halogenoalkyl, each of which has up to 4 carbon atoms and each of which is straight-chain or branched, halogenoalkyl having up to 9 identical or different halogen atoms, and $R^3$, $R^4$, $R^5$, $R^6$ and $R^7$ independently of one another represent hydrogen, fluorine, chlorine, bromine, iodine or nitro, or alkyl, alkoxy, alkylsulphonyl or alkoxycarbonyl, each of which has up to 4 carbon atoms in the particular alkyl parts and each of which is straight-chain or branched, or represent a radical $-(X')_n-R^9$, wherein X' represents oxygen, sulphur, sulphinyl or sulphonyl, n represents 0 or 1 and $R^9$ represents straight-chain or branched halogenoalkyl with up to 4 carbon atoms and up to 9 identical or different halogen atoms, with the proviso that at least one of the radicals $R^3$, $R^4$, $R^5$, $R^6$ or $R^7$ represents a radical $-(X')_n-R^9$, but R does not represent cyano at the same time as $R^5$ represents trifluoromethyl.

Particularly preferred compounds of the formula (I) are those in which

R represents cyano, methoxycarbonyl, ethoxycarbonyl, allyloxycarbonyl, propargyloxycarbonyl, aminocarbonyl, methylaminocarbonyl, dimethylaminocarbonyl, ethylaminocarbonyl, diethylaminocarbonyl, diallylaminocarbonyl or dipropargylaminocarbonyl, $R^1$ represents methyl, ethyl, n- or i-propyl, n-, i-, s- or t-butyl, allyl, butenyl, propargyl or butinyl, each of which is optionally mono-, di- or tri-substituted by identical or different substituents, possible substituents being: fluorine, chlorine, bromine, iodine, cyano, nitro, hydroxyl, carboxyl, methoxy, ethoxy, n- or i-propoxy, methoxycarbonyl, ethoxycarbonyl, n- or i-propoxycarbonyl, n-, i-, s- or t-butoxycarbonyl, aminocarbonyl, N-methylaminocarbonyl, N-ethylaminocarbonyl, N,N-dimethylaminocarbonyl, N,N-diethylaminocarbonyl, N,N-diallylaminocarbonyl, N-methyl-N-ethylaminocarbonyl, N-methyl-N-propylaminocarbonyl, N-methyl-N-allylaminocarbonyl, N-methyl-N-propargylaminocarbonyl, N-methyl-N-methoxyaminocarbonyl, N-methylsulphonylaminocarbonyl, N-ethylsulphonylaminocarbonyl, pyrrolidin-1-ylcarbonyl, piperidin-1-ylcarbonyl, morpholin-4-ylcarbonyl and perhydroazepin-1-yl-carbonyl; or represents cyclopropyl, cyclopentyl, cyclohexyl or cycloheptyl, each of which is optionally mono- , di-, tri-, tetra- or penta-substituted by identical or different substituents from the group comprising chlorine, methyl and ethyl, R² independently of R¹ represents the same radicals as R¹, and additionally represents hydrogen or a radical

wherein

X represents oxygen or sulphur and

R⁸ represents hydrogen, methyl, ethyl, n- or i-propyl, allyl, propargyl, butenyl, methoxymethyl, ethoxymethyl, methoxyethyl, ethoxyethyl, methylthiomethyl, methoxy, ethoxy, methylthio, ethylthio, methylamino, ethylamino, dimethylamino, trifluoromethyl, trichloroethyl, dichlorofluoroethyl, difluorochloroethyl, chloromethyl, iodomethyl, bromomethyl, dichloromethyl, 1-chloroethyl, 2-chloroethyl, 2-bromoethyl or heptafluoro-n-propyl, or represents cyclopropyl, cyclopentyl or cyclohexyl, each of which is optionally mono-, di-, tri- or tetra-substituted by identical or different substituents from the group comprising fluorine, chlorine, bromine, methyl and trifluoromethyl, or represents phenyl, phenoxy, phenylthio or phenylamino, each of which is optionally mono-, di- or tri-substituted by identical or different substituents from the group comprising methyl, methoxy, chlorine and trifluoromethyl, and R³, R⁴, R⁵, R⁶ and R⁷ independently of one another represent hydrogen, fluorine, chlorine, bromine, cyano, nitro, methyl, ethyl, n- or i-propyl, methoxy, ethoxy, methylsulphonyl, methoxycarbonyl or ethoxycarbonyl, or represent a radical —(X')ₙ—R⁹, wherein X' represents oxygen, sulphur, sulphinyl or sulphonyl, n represents 0 or 1 and R⁹ represents trifluoromethyl, trichloromethyl, dichlorofluoromethyl, difluorochloromethyl, dichloromethyl, chloromethyl, difluoromethyl, pentafluoroethyl, tetrafluoroethyl, trifluorochloroethyl, trifluoroethyl, difluorodichloroethyl, trifluorodichloroethyl or pentachloroethyl, with the proviso that at least one of the radicals R³, R⁴, R⁵, R⁶ or R⁷ represents a radical —(X')ₙ—R⁹, but R does not represent cyano at the same time as R⁵ represents trifluoromethyl.

The following compounds of the general formula (I) may be mentioned specifically, in addition to the compounds mentioned in the preparation examples:

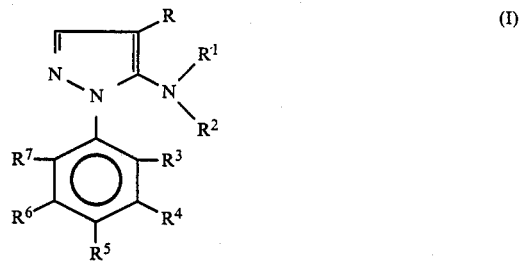

TABLE 1

| R | R¹ | R² | R³ | R⁴ | R⁵ | R⁶ | R⁷ |
|---|---|---|---|---|---|---|---|
| CN | CH₃ | H | F | H | OCF₃ | H | H |
| CN | CH₃ | H | F | H | OCF₃ | H | F |
| CN | CH₃ | H | F | F | OCF₃ | F | F |
| CN | CH₃ | H | Cl | H | OCF₃ | H | H |
| CN | CH₃ | H | Cl | H | OCF₃ | H | Cl |
| CN | CH₃ | H | Cl | Cl | OCF₃ | H | H |
| CN | CH₃ | H | Cl | H | OCF₃ | H | F |
| CN | CH₃ | H | Br | H | OCF₃ | H | H |
| CN | CH₃ | H | Br | H | OCF₃ | H | Br |
| CN | C₂H₅ | F | H | H | OCF₃ | H | H |
| CN | C₂H₅ | H | F | H | OCF₃ | H | F |
| CN | C₂H₅ | H | F | F | OCF₃ | F | F |
| CN | C₂H₅ | CH₃ | Cl | H | OCF₃ | H | H |
| CN | C₂H₅ | H | Cl | Cl | OCF₃ | H | H |
| CN | C₂H₅ | H | Cl | H | OCF₃ | H | F |
| CN | C₂H₅ | H | Br | H | OCF₃ | H | H |
| CN | C₂H₅ | H | Br | H | OCF₃ | H | Br |
| CN | C₂H₅ | CH₃ | Cl | H | OCF₃ | H | Cl |
| CN | ▷◁H | H | F | H | OCF₃ | H | H |
| CN | ▷◁H | CH₃ | F | H | OCF₃ | H | F |
| CN | ▷◁H | H | F | F | OCF₃ | F | F |
| CN | ▷◁H | H | Cl | H | OCF₃ | H | H |
| CN | ▷◁H | H | Cl | H | OCF₃ | H | Cl |

TABLE 1-continued

| R | R¹ | R² | R³ | R⁴ | R⁵ | R⁶ | R⁷ |
|---|---|---|---|---|---|---|---|
| CN | cyclopropyl-H | H | Cl | Cl | OCF₃ | H | H |
| CN | cyclopropyl-H | H | Cl | H | OCF₃ | H | F |
| CN | cyclopropyl-H | H | Br | H | OCF₃ | H | H |
| CN | cyclopropyl-H | H | Br | H | OCF₃ | H | Br |
| CN | CH₃ | H | Cl | H | SCH₂CF₃ | H | H |
| CN | CH₃ | H | Cl | H | SCH₂CF₃ | H | Cl |
| CN | CH₃ | H | Br | H | SCH₂CF₃ | H | H |
| CN | CH₃ | H | Br | H | SCH₂CF₃ | H | Br |
| CN | CH₃ | H | Cl | Cl | SCH₂CF₃ | H | H |
| CN | C₂H₅ | H | Cl | H | SCH₂CF₃ | H | H |
| CN | C₂H₅ | H | Cl | H | SCH₂CF₃ | H | Cl |
| CN | C₂H₅ | H | Br | H | SCH₂CF₃ | H | H |
| CN | C₂H₅ | H | Br | H | SCH₂CF₃ | H | Br |
| CN | C₂H₅ | H | Cl | Cl | SCH₂CF₃ | H | H |
| CN | cyclopropyl-H | H | Cl | H | SCH₂CF₃ | H | H |
| CN | cyclopropyl-H | H | Cl | H | SCH₂CF₃ | H | Cl |
| CN | cyclopropyl-H | H | Br | H | SCH₂CF₃ | H | H |
| CN | cyclopropyl-H | H | Br | H | SCH₂CF₃ | H | Br |
| CN | cyclopropyl-H | H | Cl | Cl | SCH₂CF₃ | H | H |
| CN | CH₃OCH₂ | H | Cl | H | SCH₂CF₃ | H | H |
| CN | CH₃OCH₂ | H | Cl | H | SCH₂CF₃ | H | Cl |
| CN | CH₃OCH₂ | H | Br | H | SCH₂CF₃ | H | H |
| CN | CH₃OCH₂ | H | Br | H | SCH₂CF₃ | H | Br |
| CN | CH₃OCH₂ | H | Cl | Cl | SCH₂CF₃ | H | H |
| CN | CH₃ | H | Cl | H | OCH₂CF₃ | H | H |
| CN | CH₃ | H | Cl | H | OCH₂CF₃ | H | Cl |
| CN | CH₃ | H | Br | H | OCH₂CF₃ | H | H |
| CN | CH₃ | H | Br | H | OCH₂CF₃ | H | Br |
| CN | C₂H₅ | H | Cl | H | OCH₂CF₃ | H | H |
| CN | C₂H₅ | H | Cl | H | OCH₂CF₃ | H | Cl |
| CN | C₂H₅ | H | Br | H | OCH₂CF₃ | H | H |
| CN | C₂H₅ | H | Br | H | OCH₂OCF₃ | H | Br |
| CN | cyclopropyl-H | H | Cl | H | OCH₂CF₃ | H | H |
| CN | cyclopropyl-H | H | Cl | H | OCH₂CF₃ | H | Cl |
| CN | cyclopropyl-H | H | Br | H | OCH₂CF₃ | H | H |
| CN | C₂H₅ | H | Cl | H | SCF₃ | H | H |
| CN | C₂H₅ | H | Cl | H | SCF₃ | H | Cl |
| CN | C₂H₅ | H | Cl | H | SCF₃ | H | F |
| CN | C₂H₅ | H | Br | H | SCF₃ | H | H |
| CN | cyclopropyl-H | H | F | H | SCF₃ | H | H |

TABLE 1-continued

| R | R¹ | R² | R³ | R⁴ | R⁵ | R⁶ | R⁷ |
|---|---|---|---|---|---|---|---|
| CN | cyclopropyl-H | H | F | H | SCF₃ | H | F |
| CN | cyclopropyl-H | H | F | F | SCF₃ | F | F |
| CN | cyclopropyl-H | H | Cl | H | SCF₃ | H | H |
| CN | cyclopropyl-H | H | Cl | H | SCF₃ | H | Cl |
| CN | cyclopropyl-H | H | Cl | Cl | SCF₃ | H | H |
| CN | cyclopropyl-H | H | Cl | H | SCF₃ | H | F |
| CN | cyclopropyl-H | H | Br | H | SCF₃ | H | H |
| CN | cyclopropyl-H | H | Br | H | SCF₃ | H | Br |
| CN | CH₃ | H | CF₃ | H | SO₂CH₃ | H | H |
| CN | CH₃ | H | CF₃ | H | SO₂CH₃ | H | H |
| CN | CH₃ | H | CF₃ | H | SCF₃ | H | H |
| CN | CH₃ | H | OCF₃ | H | OCF₃ | H | H |
| CN | C₂H₅ | H | CF₃ | H | SO₂CH₃ | H | H |
| CN | C₂H₅ | H | CF₃ | H | SO₂CH₃ | H | H |
| CN | C₂H₅ | H | CF₃ | H | SCF₃ | H | H |
| CN | C₂H₅ | H | OCF₃ | H | OCF₃ | H | H |
| CN | cyclopropyl-H | H | CF₃ | H | SO₂CH₃ | H | H |
| CN | cyclopropyl-H | CH₃ | CF₃ | H | SO₂CH₃ | H | H |
| CN | cyclopropyl-H | C₂H₅ | CF₃ | H | SCF₃ | H | H |
| CN | cyclopropyl-H | C₃H₇ | OCF₃ | H | OCF₃ | H | H |
| CN | CH₃ | CH₃ | Cl | H | SCHF₂ | H | H |
| CN | CH₃ | C₂H₅ | Cl | H | SCH₂F | H | Cl |
| CN | CH₃ | C₃H₇ | Br | H | SCHF₂ | H | H |
| CN | CH₃ | H | Br | H | SCHF₂ | H | Br |
| CN | C₂H₅ | CH₃ | Cl | H | SCH₂F | H | H |
| CN | C₂H₅ | C₂H₅ | Cl | H | SCHF₂ | H | Cl |
| CN | C₂H₅ | C₂H₅ | Br | H | SCHF₂ | H | H |
| CN | C₂H₅ | C₃H₇ | Br | H | SCHF₂ | H | Br |
| CN | cyclopropyl-H | C₃H₇ | Cl | H | SCHF₂ | H | H |
| CN | cyclopropyl-H | H | Cl | H | SCHF₂ | H | Cl |
| CN | cyclopropyl-H | CH₃ | Br | H | SCHF₂ | H | H |

TABLE 1-continued

| R | R¹ | R² | R³ | R⁴ | R⁵ | R⁶ | R⁷ |
|---|---|---|---|---|---|---|---|
| CN | cyclopropyl | $C_3H_7$ | Br | H | $SCHF_2$ | H | Br |
| CN | $CH_3$ | H | Cl | H | $SCF_2CHF_2$ | H | H |
| CN | $CH_3$ | H | Cl | H | $SCF_2CHF_2$ | H | Cl |
| CN | $CH_3$ | H | Br | H | $SCF_2CHF_2$ | H | H |
| CN | $CH_3$ | $CH_3$ | Br | H | $SCF_2CHF_2$ | H | Br |
| CN | $C_2H_5$ | $CH_3$ | Cl | H | $SCF_2CHF_2$ | H | H |
| CN | $C_2H_5$ | $CH_3$ | Cl | H | $SCF_2CHF_2$ | H | Cl |
| CN | $C_2H_5$ | $C_2H_5$ | Br | H | $SCF_2CHF_2$ | H | H |
| CN | $C_2H_5$ | $C_2H_5$ | Br | H | $SCF_2CHF_2$ | H | Br |
| CN | cyclopropyl | $C_2H_5$ | Cl | H | $SCF_2CHF_2$ | H | H |
| CN | cyclopropyl | $C_3H_7$ | Cl | H | $SCF_2CHF_2$ | H | Cl |
| CN | cyclopropyl | $C_3H_7$ | Br | H | $SCF_2CHF_2$ | H | H |
| CN | cyclopropyl | $C_3H_7$ | Br | H | $SCF_2CHF_2$ | H | Br |
| CN | $CH_3$ | H | Cl | H | $SCF_2CHFCl$ | H | H |
| CN | $CH_3$ | H | Cl | H | $SCF_2CHFCl$ | H | Cl |
| CN | $CH_3$ | H | Br | H | $SCF_2CHFCl$ | H | H |
| CN | $CH_3$ | H | Br | H | $SCF_2CHFCl$ | H | Br |
| CN | $C_2H_5$ | H | Cl | H | $SCF_2CHFCl$ | H | H |
| CN | $C_2H_5$ | H | Cl | H | $SCF_2CHFCl$ | H | Cl |
| CN | $C_2H_5$ | H | Br | H | $SCF_2CHFCl$ | H | H |
| CN | $C_2H_5$ | H | Br | H | $SCF_2CHFCl$ | H | Br |
| CN | cyclopropyl | H | Cl | H | $SCF_2CHFCl$ | H | H |
| CN | cyclopropyl | H | Cl | H | $SCF_2CHFCl$ | H | Cl |
| CN | cyclopropyl | H | Br | H | $SCF_2CHFCl$ | H | H |
| CN | cyclopropyl | H | Br | H | $SCF_2CHFCl$ | H | Br |
| CN | $ClCH_2$ | $CH_3$ | Cl | H | $SCF_3$ | H | H |
| CN | $ClCH_2$ | $CH_3$ | Cl | H | $OCF_3$ | H | Cl |
| CN | $ClCH_2$ | $C_2H_5$ | Br | H | $OCF_3$ | H | H |
| CN | $ClCH_2$ | H | Br | H | $OCF_3$ | H | Br |
| CN | $CH_3OCH_2$ | $C_3H_7$ | Cl | H | $OCF_3$ | H | H |
| CN | $CH_3OCH_2$ | H | Cl | H | $OCF_3$ | H | Cl |
| CN | $ClCH_2$ | H | Cl | H | $SCF_3$ | H | H |
| CN | $ClCH_2$ | H | Cl | H | $SCF_3$ | H | Cl |
| CN | $ClCH_2$ | H | Br | H | $SCF_3$ | H | H |
| CN | $CH_3$ | $CH_3$ | Cl | H | $S(O)CF_3$ | H | H |
| CN | $CH_3$ | $CH_3$ | Cl | H | $S(O)CF_3$ | H | Cl |
| CN | $CH_3$ | $C_3H_7$ | Br | H | $S(O)CF_3$ | H | Br |
| CN | $CH_3$ | $C_2H_5$ | Br | H | $S(O)CF_3$ | H | H |
| CN | $CH_3$ | $C_3H_7$ | $CF_3$ | H | $S(O)CF_3$ | H | H |
| CN | $CH_3$ | H | $CF_3$ | H | $S(O)CF_3$ | H | Cl |
| CN | $C_2H_5$ | H | Cl | H | $S(O)CF_3$ | H | H |
| CN | $C_2H_5$ | $CH_3$ | Cl | H | $S(O)CF_3$ | H | Cl |
| CN | $C_2H_5$ | $CH_3$ | Br | H | $S(O)CF_3$ | H | Br |
| CN | $C_2H_5$ | H | Br | H | $S(O)CF_3$ | H | H |
| CN | $C_2H_5$ | H | $CF_3$ | H | $S(O)CF_3$ | H | H |
| CN | $C_2H_5$ | H | $CF_3$ | H | $S(O)CF_3$ | H | Cl |
| CN | cyclopropyl | H | Cl | H | $S(O)CF_3$ | H | H |

TABLE 1-continued

| R | R¹ | R² | R³ | R⁴ | R⁵ | R⁶ | R⁷ |
|---|---|---|---|---|---|---|---|
| CN | cyclopropyl-H | H | Cl | H | S(O)CF$_3$ | H | Cl |
| CN | cyclopropyl-H | H | Br | H | S(O)CF$_3$ | H | Br |
| CN | cyclopropyl-H | H | Br | H | S(O)CF$_3$ | H | H |
| CN | cyclopropyl-H | H | CF$_3$ | H | S(O)CF$_3$ | H | H |
| CN | cyclopropyl-H | H | CF$_3$ | H | S(O)CF$_3$ | H | Cl |
| CN | CH$_3$ | H | Cl | H | OCF$_2$CHFCl | H | H |
| CN | CH$_3$ | H | Cl | H | OCF$_2$CHFCl | H | Cl |
| CN | CH$_3$ | CH$_3$ | Br | H | OCF$_2$CHFCl | H | H |
| CN | CH$_3$ | C$_2$H$_5$ | Br | H | OCF$_2$CHFCl | H | Br |
| CN | C$_2$H$_5$ | C$_3$H$_7$ | Cl | H | OCF$_2$CHFCl | H | H |
| CN | C$_2$H$_5$ | C$_2$H$_5$ | Cl | H | OCF$_2$CHFCl | H | Cl |
| CN | C$_2$H$_5$ | CH$_3$ | Br | H | OCF$_2$CHFCl | H | H |
| CN | C$_2$H$_5$ | H | Br | H | OCF$_2$CHFCl | H | Br |
| CN | cyclopropyl-H | H | Cl | H | OCF$_2$CHFCl | H | H |
| CN | cyclopropyl-H | H | Cl | H | OCF$_2$CHFCl | H | Cl |
| CN | cyclopropyl-H | H | Br | H | OCF$_2$CHFCl | H | H |
| CN | cyclopropyl-H | H | Br | H | OCF$_2$CHFCl | H | Br |
| CN | CH$_3$ | CH$_3$ | Cl | H | OCF$_2$CHCl$_2$ | H | H |
| CN | CH$_3$ | C$_2$H$_5$ | Cl | H | OCF$_2$CHCl$_2$ | H | Cl |
| CN | CH$_3$ | C$_3$H$_7$ | Br | H | OCF$_2$CHCl$_2$ | H | H |
| CN | CH$_3$ | H | Br | H | OCF$_2$CHCl$_2$ | H | Br |
| CN | C$_2$H$_5$ | H | Cl | H | OCF$_2$CHCl$_2$ | H | H |
| CN | C$_2$H$_5$ | H | Cl | H | OCF$_2$CHCl$_2$ | H | Cl |
| CN | C$_2$H$_5$ | H | Br | H | OCF$_2$CHCl$_2$ | H | H |
| CN | C$_2$H$_5$ | CH$_3$ | Br | H | OCF$_2$CHCl$_2$ | H | Br |
| CN | cyclopropyl-H | C$_2$H$_5$ | Cl | H | OCF$_2$CHCl$_2$ | H | H |
| CN | cyclopropyl-H | C$_3$H$_7$ | Cl | H | OCF$_2$CHCl$_2$ | H | Cl |
| CN | cyclopropyl-H | H | Br | H | OCF$_2$CHCl$_2$ | H | H |
| CN | cyclopropyl-H | CH$_3$ | Br | H | OCF$_2$CHCl$_2$ | H | Br |
| CN | CH$_3$ | C$_2$H$_5$ | Cl | H | OCF$_2$CHF$_2$ | H | H |
| CN | CH$_3$ | C$_3$H$_7$ | Cl | H | OCF$_2$CHF$_2$ | H | Cl |
| CN | CH$_3$ | H | Br | H | OCF$_2$CHF$_2$ | H | H |
| CN | CH$_3$ | H | Br | H | OCF$_2$CHF$_2$ | H | Br |
| CN | C$_2$H$_5$ | H | Cl | H | OCF$_2$CHF$_2$ | H | H |
| CN | C$_2$H$_5$ | H | Cl | H | OCF$_2$CHF$_2$ | H | Cl |
| CN | C$_2$H$_5$ | H | Br | H | OCF$_2$CHF$_2$ | H | H |
| CN | C$_2$H$_5$ | H | Br | H | OCF$_2$CHF$_2$ | H | Br |

TABLE 1-continued

| R | R¹ | R² | R³ | R⁴ | R⁵ | R⁶ | R⁷ |
|---|---|---|---|---|---|---|---|
| CN | cyclopropyl-H | H | Cl | H | OCF$_2$CHF$_2$ | H | H |
| CN | cyclopropyl-H | H | Cl | H | OCF$_2$CHF$_2$ | H | Cl |
| CN | cyclopropyl-H | H | Br | H | OCF$_2$CHF$_2$ | H | H |
| CN | cyclopropyl-H | H | Br | H | OCF$_2$CHF$_2$ | H | Br |
| CN | CH$_3$ | CH$_3$ | CF$_3$ | H | SO$_2$CH$_3$ | H | H |
| CN | C$_2$H$_5$ | C$_2$H$_5$ | Br | H | SO$_2$CF$_3$ | H | H |
| CN | C$_2$H$_5$ | C$_2$H$_5$ | Br | H | SO$_2$CF$_3$ | H | Br |
| CN | C$_2$H$_5$ | CH$_3$ | CF$_3$ | H | SO$_2$CF$_3$ | H | H |
| CN | cyclopropyl-H | CH$_3$ | Cl | H | SO$_2$CF$_3$ | H | H |
| CN | cyclopropyl-H | CH$_3$ | Cl | H | SO$_2$CF$_3$ | H | Cl |
| CN | cyclopropyl-H | H | Br | H | SO$_2$CF$_3$ | H | H |
| CN | cyclopropyl-H | H | Br | H | SO$_2$CF$_3$ | H | Br |
| CN | cyclopropyl-H | H | CF$_3$ | H | SO$_2$CF$_3$ | H | H |
| CN | CH$_3$ | H | F | H | SCCl$_2$F | H | H |
| CN | CH$_3$ | H | F | H | SCCl$_2$F | H | F |
| CN | CH$_3$ | H | F | F | SCCl$_2$F | F | F |
| CN | CH$_3$ | CH$_3$ | Cl | H | SCCl$_2$F | H | H |
| CN | CH$_3$ | CH$_3$ | Cl | H | SCCl$_2$F | H | Cl |
| CN | CH$_3$ | CH$_3$ | Cl | H | SCCl$_2$F | H | F |
| CN | CH$_3$ | C$_2$H$_5$ | Br | H | SCCl$_2$F | H | H |
| CN | CH$_3$ | C$_2$H$_5$ | Br | H | SCCl$_2$F | H | Br |
| CN | C$_2$H$_5$ | C$_2$H$_5$ | F | H | SCCl$_2$F | H | H |
| CN | C$_2$H$_5$ | C$_2$H$_5$ | F | H | SCCl$_2$F | H | F |
| CN | C$_2$H$_5$ | C$_2$H$_5$ | F | H | SCCl$_2$F | F | F |
| CN | C$_2$H$_5$ | CH$_3$ | Cl | H | SCCl$_2$F | H | H |
| CN | C$_2$H$_5$ | CH$_3$ | Cl | H | SCCl$_2$F | H | Cl |
| CN | C$_2$H$_5$ | H | Cl | H | SCCl$_2$F | H | F |
| CN | C$_2$H$_5$ | H | Br | H | SCCl$_2$F | H | H |
| CN | C$_2$H$_5$ | H | Br | H | SCCl$_2$F | H | Br |
| CN | cyclopropyl-H | H | F | H | SCCl$_2$F | H | H |
| CN | cyclopropyl-H | H | F | H | SCCl$_2$F | H | F |
| CN | cyclopropyl-H | CH$_3$ | F | F | SCCl$_2$F | F | F |
| CN | cyclopropyl-H | CH$_3$ | Cl | H | SCCl$_2$F | H | H |
| CN | cyclopropyl-H | CH$_3$ | Cl | H | SCCl$_2$F | H | Cl |
| CN | cyclopropyl-H | C$_2$H$_5$ | Cl | H | SCCl$_2$F | H | F |

TABLE 1-continued

| R | R¹ | R² | R³ | R⁴ | R⁵ | R⁶ | R⁷ |
|---|---|---|---|---|---|---|---|
| CN | cyclopropyl-H | C₂H₅ | Br | H | SCCl₂F | H | H |
| CN | cyclopropyl-H | C₂H₅ | Br | H | SCCl₂F | H | Br |
| CN | CH₃ | H | F | H | OCHF₂ | H | H |
| CN | CH₃ | H | F | H | OCHF₂ | H | F |
| CN | CH₃ | H | F | F | OCHF₂ | F | F |
| CN | CH₃ | H | Cl | H | OCHF₂ | H | H |
| CN | CH₃ | H | Cl | H | OCHF₂ | H | Cl |
| CN | CH₃ | H | Cl | H | OCHF₂ | H | F |
| CN | CH₃ | H | Br | H | OCHF₂ | H | H |
| CN | CH₃ | H | Br | H | OCHF₂ | H | Br |
| CN | C₂H₅ | H | F | H | OCHF₂ | H | H |
| CN | C₂H₅ | H | F | H | OCHF₂ | H | F |
| CN | C₂H₅ | H | F | F | OCHF₂ | F | F |
| CN | C₂H₅ | H | Cl | H | OCHF₂ | H | H |
| CN | C₂H₅ | H | Cl | H | OCHF₂ | H | Cl |
| CN | C₂H₅ | H | Cl | H | OCHF₂ | H | F |
| CN | C₂H₅ | H | Br | H | OCHF₂ | H | F |
| CN | C₂H₅ | H | Br | H | OCHF₂ | H | Br |
| CN | cyclopropyl-H | H | F | H | OCHF₂ | H | H |
| CN | cyclopropyl-H | H | F | H | OCHF₂ | H | F |
| CN | cyclopropyl-H | H | F | F | OCHF₂ | F | F |
| CN | cyclopropyl-H | CH₃ | Cl | H | OCHF₂ | H | H |
| CN | cyclopropyl-H | CH₃ | Cl | H | OCHF₂ | H | Cl |
| CN | cyclopropyl-H | CH₃ | Cl | H | OCH₂F | H | F |
| CN | cyclopropyl-H | C₂H₅ | Br | H | OCH₂F | H | H |
| CN | cyclopropyl-H | C₂H₅ | Br | H | OCHF₂ | H | Br |
| CN | Cl,Cl-cyclopropyl-CH₃ | C₂H₅ | Cl | H | OCF₃ | H | H |
| CN | Cl,Cl-cyclopropyl-CH₃ | C₂H₅ | Cl | H | OCF₃ | H | Cl |
| CN | Cl,Cl-cyclopropyl-CH₃ | C₂H₅ | Cl | H | SCF₃ | H | H |

TABLE 1-continued

| R | R¹ | R² | R³ | R⁴ | R⁵ | R⁶ | R⁷ |
|---|---|---|---|---|---|---|---|
| CN | Cl,Cl-cyclopropyl-CH₃ | C₃H₇ | Cl | H | SCF₃ | H | Cl |
| CN | Cl,Cl-cyclopropyl-CH₃ | C₃H₇ | Cl | H | SO₂CF₃ | H | H |
| CN | Cl,Cl-cyclopropyl-CH₃ | H | Cl | H | SO₂CF₃ | H | Cl |
| CN | cyclopropyl-H | H | Br | H | OCH₂CF₃ | H | Br |
| CN | CH₃OCH₂ | H | Cl | H | OCH₂CF₃ | H | H |
| CN | CH₃OCH₂ | H | Cl | H | OCH₂CF₃ | H | Cl |
| CN | CH₃OCH₂ | H | Br | H | OCH₂CF₃ | H | H |
| CN | CH₃OCH₂ | H | Br | H | OCH₂CF₃ | H | Br |
| CN | CH₃ | H | SCF₃ | H | Cl | H | H |
| CN | C₂H₅ | H | SCF₃ | H | Cl | H | H |
| CN | CH₃ | H | SCF₃ | H | Cl | H | Cl |
| CN | C₂H₅ | H | SCF₃ | H | Cl | H | Cl |
| CN | CH₃ | H | Cl | H | SO₂CH₂CF₃ | H | Cl |
| CN | CH₃ | H | Cl | H | SO₂CH₂CF₃ | H | Cl |
| CN | C₂H₅ | H | Cl | H | SO₂CH₂CF₃ | H | Cl |
| CN | C₂H₅ | H | Cl | H | SO₂CH₂CF₃ | H | Cl |
| CN | CH₃ | H | F | H | SCF₃ | H | H |
| CN | CH₃ | H | F | H | SCF₃ | H | F |
| CN | CH₃ | H | F | F | SCF₃ | F | F |
| CN | CH₃ | H | Cl | H | SCF₃ | H | H |
| CN | CH₃ | H | Cl | H | SCF₃ | H | Cl |
| CN | CH₃ | H | Cl | Cl | SCF₃ | H | H |
| CN | CH₃ | H | Cl | H | SCF₃ | H | F |
| CN | CH₃ | H | Br | H | SCF₃ | H | H |
| CN | CH₃ | H | Br | H | SCF₃ | H | Br |
| CN | C₂H₅ | H | F | H | SCF₃ | H | H |
| CN | C₂H₅ | H | F | H | SCF₃ | H | F |
| CN | C₂H₅ | H | F | H | SCF₃ | F | F |
| CN | n-C₃H₇ | H | Cl | H | OCF₃ | H | H |
| CN | n-C₃H₇ | H | Cl | H | OCF₃ | H | Cl |
| CN | i-C₃H₇ | H | Cl | H | OCF₃ | H | H |
| CN | i-C₃H₇ | H | Cl | H | OCF₃ | H | Cl |
| CN | C₂H₅ | C₂H₅ | Cl | H | OCF₃ | H | H |
| CN | C₂H₅ | C₂H₅ | Cl | H | OCF₃ | H | Cl |
| CN | CH₃ | CH₃ | Cl | H | OCF₃ | H | H |
| CN | CH₃ | CH₃ | Cl | H | OCF₃ | H | Cl |
| CN | n-C₃H₇ | C₃H₇ | Cl | H | OCF₃ | H | H |
| CN | n-C₃H₇ | C₃H₇ | Cl | H | OCF₃ | H | Cl |
| CN | n-C₃H₇ | H | Cl | H | SCF₃ | H | H |
| CN | n-C₃H₇ | H | Cl | H | SCF₃ | H | Cl |
| CN | i-C₃H₇ | H | Cl | H | SCF₃ | H | H |
| CN | i-C₃H₇ | H | Cl | H | SCF₃ | H | Cl |
| CN | C₂H₅ | C₂H₅ | Cl | H | SCF₃ | H | H |
| CN | C₂H₅ | C₂H₅ | Cl | H | SCF₃ | H | Cl |
| CN | CH₃ | CH₃ | Cl | H | SCF₃ | H | H |
| CN | CH₃ | CH₃ | Cl | H | SCF₃ | H | Cl |
| CN | n-C₃H₇ | C₃H₇ | Cl | H | SCF₃ | H | H |
| CN | n-C₃H₇ | C₃H₇ | Cl | H | SCF₃ | H | Cl |
| CN | n-C₃H₇ | H | Cl | H | SO₂CF₃ | H | H |
| CN | n-C₃H₇ | H | Cl | H | SO₂CF₃ | H | Cl |
| CN | i-C₃H₇ | H | Cl | H | SO₂CF₃ | H | H |
| CN | i-C₃H₇ | H | Cl | H | SO₂CF₃ | H | Cl |
| CN | C₂H₅ | C₂H₅ | Cl | H | SO₂CF₃ | H | H |
| CN | C₂H₅ | C₂H₅ | Cl | H | SO₂CF₃ | H | Cl |
| CN | n-C₃H₇ | C₃H₇ | Cl | H | SO₂CF₃ | H | H |
| CN | n-C₃H₇ | C₃H₇ | Cl | H | SO₂CF₃ | H | Cl |
| CN | n-C₃H₇ | −C(=O)−CH₃ | Cl | H | OCF₃ | H | H |

TABLE 1-continued

| R | R¹ | R² | R³ | R⁴ | R⁵ | R⁶ | R⁷ |
|---|---|---|---|---|---|---|---|
| CN | C₂H₅ | —C(=O)—CH₃ | Cl | H | OCF₃ | H | Cl |
| CN | n-C₃H₇ | —C(=O)—CH₃ | Cl | H | SCH₃ | H | Cl |
| CN | n-C₃H₇ | —C(=O)—CH₃ | Cl | H | SO₂CF₃ | H | Cl |
| CN | n-C₃H₇ | —C(=O)—CH₃ | Cl | H | OCF₃ | H | Cl |

If, for example, 4-cyano-5-propionylamino-1-(2,6-dichloro-4-trifluoromethylthiophenyl)-pyrazole and methyl iodide are used as starting substances, the course of the reaction in process (a) according to the invention can be represented by the following equation:

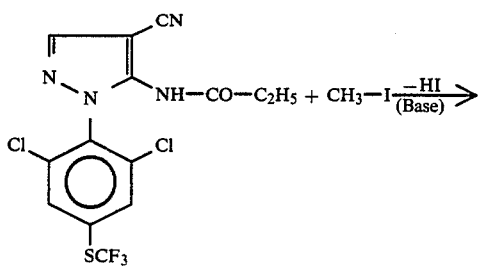

If, for example, 4-cyano-5-(N-n-propyl-N-propionylamino)-1-(2-chloro-4-trifluoromethoxyphenyl)-pyrazole and sodium hydroxide solution are used as starting substances, the course of the reaction in process (b) according to the invention can be represented by the following equation:

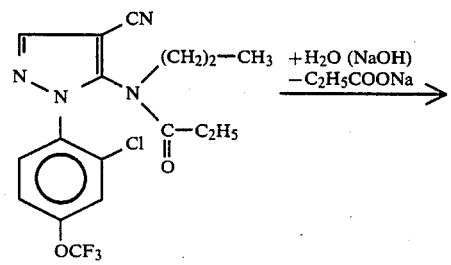

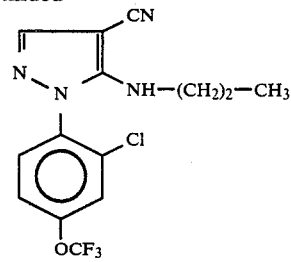

If, for example, 4-cyano-5-isopropylideneimino-1-(2-chloro-4-trifluoromethylthiophenyl)-pyrazole is used as the starting substance and sodium borohydride is used as the reducing agent, the course of the reaction in process (c) according to the invention can be represented by the following equation:

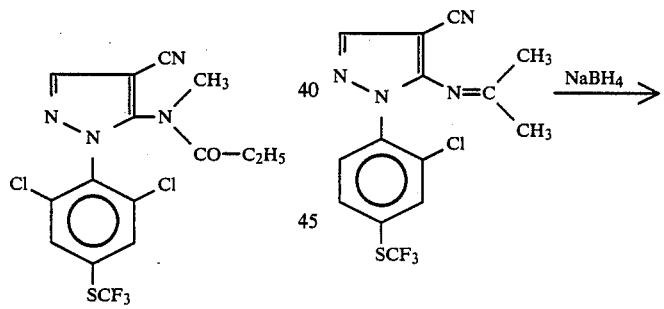

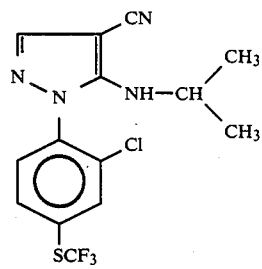

Formula (II) provides a general definition of the 5-amino-pyrazoles required as starting substances for carrying out process (a) according to the invention. In this formula (II), R, R³, R⁴, R⁵, R⁶ and R⁷ preferably represent those radicals which have already been mentioned as preferred for these substituents in connection with the description of the substances of the formula (I) according to the invention. R¹⁰ preferably represents hydrogen or a radical $$-\underset{\underset{X}{\parallel}}{C}-R^8,$$

X and $R^8$ having the same preferred meanings which have already been mentioned for these radicals in the description of the substances of the formula (I) according to the invention.

The 5-aminopyrazoles of the formula (II) are known in some cases (compare, for example, DE-OS (German Published Specification) No. 3,226,496, DE-OS (German Published Specification) No. 3,129,429 and European Patent Application No. 34,945).

They are obtained by processes which are known in principle, for example in which acrylonitrile derivatives of the formula (V)

$$C_2H_5O-CH=C\begin{smallmatrix}CN\\R\end{smallmatrix} \qquad (V)$$

in which

R has the abovementioned meaning, and phenylhydrazines of the formula (VI)

(VI) [structure: $H_2N-NH-$ phenyl with substituents $R^3, R^4, R^5, R^6, R^7$]

in which $R^3$, $R^4$, $R^5$, $R^6$ and $R^7$ have the abovementioned meaning, are either reacted initially in a first stage, if appropriate in the presence of a diluent (such as, for example, glacial acetic acid or ethanol) and if appropriate in the presence of a reaction auxiliary (such as, for example, sodium acetate) at temperatures between $-20°$ C. and $+20°$ C., to give the phenylhydrazine derivatives of the formula (VII)

(VII) [structure: phenyl with $R^3, R^4, R^5, R^6, R^7$ substituted by $-NH-NH-CH=C(CN)(R)$]

in which

R, $R^3$, $R^4$, $R^5$, $R^6$ and $R^7$ have the abovementioned meaning, and these are cyclized in a second stage, if appropriate in the presence of a diluent (such as, for example, ethylene glycol monoethyl ether) at temperatures between $+50°$ C. and $+150°$ C., or are cyclized directly in one reaction step, without isolation of the intermediate of the formula (VII), if appropriate in the presence of a diluent (such as, for example, ethylene glycol monoethyl ether or ethanol) at temperatures between $+50°$ C. and $+150°$ C., and the 5-aminopyrazoles thus obtainable, of the formula (IIa)

(IIa) [pyrazole structure with R, $NH_2$, and N-phenyl bearing $R^3, R^4, R^5, R^6, R^7$]

in which

R, $R^3$, $R^4$, $R^5$, $R^6$ and $R^7$ have the abovementioned meaning, are acylated, if appropriate, with an acylating agent of the formula (VIII)

$$R^8-\underset{\underset{X}{\parallel}}{C}-A' \qquad (VIII)$$

in which $R^8$ and X have the abovementioned meaning and

A' represents an electron-withdrawing leaving group, such as, for example, halogen, or the radical $$R^8-\underset{\underset{O}{\parallel}}{C}-O-,$$

or with an iso(thio)cyanate of the formula (IX)

$$R^{8'}-N=C=X \qquad (IX)$$

in which

X has the abovementioned meaning and $R^{8'}$ represents alkyl or optionally substituted aryl, if appropriate in the presence of a diluent (such as, for example, methylene chloride or acetonitrile) and if appropriate in the presence of an acid-binding agent (such as, for example, potassium carbonate or triethylamine) at temperatures between $-20°$ C. and $+120°$ C. (compare German Patent Application No. 33 37 543.7 corresponding to U.S. Ser. No. 659,731, filed Oct. 11, 1984, now pending; German Patent Application Nos. 34 20 985.9 and 34 23 582.5.

The acrylonitrile derivatives of the formula (V) are known (compare, for example, European Patent Application No. 34,945 or DE-OS (German Published Specification) No. 3,129,429).

The phenylhydrazines of the formula (VI) are known in most cases or they can be prepared by known processes in a simple analogous manner (compare, for example, Houben-Weyl, "Methoden der organischen Chemie" ("Methods of organic chemistry"), Volume X/2, page 203, Thieme Verlag Stuttgart, 1967), for example by reacting the known anilines of the formula (X)

(X) [aniline structure: phenyl with $R^3, R^4, R^5, R^6, R^7$ and $-NH_2$]

in which $R^3$, $R^4$, $R^5$, $R^6$ and $R^7$ have the abovementioned meaning, with sodium nitrite in the presence of an acid (such as, for example, sulphuric acid) and then with tin-II chloride, also in the presence of an acid (such as, for example, hydrochloric acid), at temperatures between $-20°$ C. and $+80°$ C.

The acylating agents of the formula (VIII), the iso(thio)cyanates of the formula (IX) and the anilines of the formula (X) are generally known compounds of organic chemistry.

Formula (III) provides a general definition of the alkylating agents furthermore required as starting substances for carrying out process (a) according to the invention. In this formula (III), $R^1$ preferably represents those radicals which have already been mentioned as preferred for these substituents in the description of the substances of the formula (I) according to the invention. A preferably represents halogen, in particular chlorine, bromine, or iodine, or represents alkylsulphonyloxy, alkoxysulphonyloxy or arylsulphonyloxy, each of which is optionally substituted, such as, for example, methanesulphonyloxy, methoxysulphonyloxy or p-toluenesulphonyloxy. The alkylating agents of the formula (III) are generally known compounds of organic chemistry. Formula (Ia) provides a general definition of the 5-acylamino-pyrazoles required as starting substances for carrying out process (b) according to the invention. In this formula (Ia), R, $R^1$, $R^3$, $R^4$, $R^5$, $R^6$, $R^7$ and $R^8$ preferably represent those radicals which have already been mentioned as preferred for these substituents in the description of the substances of the formula (I) according to the invention.

The 5-acylamino-pyrazoles of the formula (Ia) are compounds according to the invention and are obtainable with the aid of process (a) according to the invention.

Formula (IV) provides a general definition of the azomethines required as starting substances for carrying out process (c) according to the invention. In this formula (IV), R, $R^3$, $R^4$, $R^5$, $R^6$ and $R^7$ preferably represent those radicals which have already been mentioned as preferred for these substituents in the description of the substances of the formula (I) according to the invention. $R^{11}$ preferably represents alkyl, alkenyl or alkinyl, each of which has up to 7 carbon atoms and each of which is straight-chain or branched and optionally monosubstituted or polysubstituted by identical or different substituents, and in particular represents methyl, ethyl, n- or i-propyl, n-, i-, s- or t-butyl, allyl, butenyl, propargyl or butinyl, possible substituents being: halogen, cyano, hydroxyl, carboxyl and alkoxy and alkoxycarbonyl, each of which has up to 6 carbon atoms and each of which is straight-chain or branched. $R^{12}$ independently of $R^{11}$ preferably represents the same radicals as $R^{11}$, and also represents hydrogen.

The azomethines of the formula (IV) are not yet known. They are obtained by a process in which 5-aminopyrazoles of the formula (IIa)

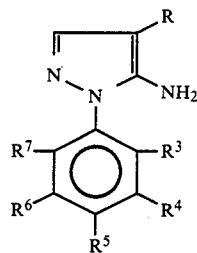

in which

R, $R^3$, $R^4$, $R^5$, $R^6$ and $R^7$ have the abovementioned meaning, are reacted with aldehydes or ketones of the formula (XI)

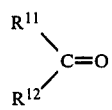

in which $R^{11}$ and $R^{12}$ have the abovementioned meaning, if appropriate in the presence of a diluent (such as, for example, methanol or ethanol) and if appropriate in the presence of a catalyst (such as, for example, hydrochloric acid or sulphuric acid), at temperatures between $+20°$ C. and $+120°$C.

The aldehydes or ketones of the formula (XI) are likewise generally known compounds of organic chemistry.

Possible diluents for carrying out process (a) according to the invention are inert organic solvents. These include, in particular, aliphatic or aromatic, optionally halogenated hydrocarbons, such as, for example, benzine, benzene, toluene, xylene, chlorobenzene, petroleum ether, hexane, cyclohexane, methylene chloride, chloroform or carbon tetrachloride, ethers, such as diethyl ether, dioxane, tetrahydrofuran or ethylene glycol dimethyl or diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric acid triamide, esters, such as ethyl acetate, or sulphoxides, such as dimethylsulphoxide.

If appropriate, process (a) according to the invention can also be carried out in a two-phase system, such as, for example, water/toluene or water/methylene chloride, if appropriate in the presence of a phase transfer catalyst. Examples which may be mentioned of such catalysts are: tetrabutylammonium iodide, tetrabutylammonium bromide, tributyl-methylphosphonium bromide, trimethyl-$C_{13}$/$C_{15}$-alkylammonium chloride, dibenzylammonium methylsulphate, dimethyl-$C_{12}$/$C_{14}$-alkyl-benzylammonium chloride, tetrabutylammonium hydroxide, 15-crown-5, 18-crown-6, triethylbenzylammonium chloride and trimethylbenzylammonium chloride.

Possible acid-binding agents for carrying out preparation process (a) are all the inorganic and organic bases which can usually be employed. Bases which are preferably used are alkali metal hydrides, hydroxides, amides, carbonates or bicarbonates, such as, for example, sodium hydride, sodium amide, sodium hydroxide, sodium carbonate or sodium bicarbonate, or tertiary amines, such as, for example, triethylamine, N,N-dimethylaniline, pyridine, 4-(N,N-dimethylamino)-pyridine, diazabicyclooctane (DABCO), diazabicyclononene (DBN) or diazabicycloundecene (DBU).

The reaction temperatures can be varied within a substantial range in carrying out preparation process (a). In general, the reaction is carried out between $<20°$ C. and $+150°$, preferably between $0°$ C. and $+100°$ C.

For carrying out preparation process (a), in general 1.0 to 20.0 moles, preferably 1.0 to 15.0 moles, of alkylating agent of the formula (III) and, if appropriate, 1.0 to 3.0 moles, preferably 1.0 to 2.0 moles, of acid-binding agent, as well as 0.01 to 1.0 mole of phase transfer catalyst are employed per mole of 5-aminopyrazole of the formula (II). The reaction is carried out and the reaction products of the formula (I) are worked up and isolated in the generally customary manner.

Possible diluents for carrying out process (b) according to the invention are likewise inert organic or inorganic solvents. The organic solvents listed for process (a) may be mentioned in particular. Alcohols, such as methanol or ethanol, or mixtures thereof with water are particularly preferred.

Process (b) is carried out either in the presence of a strong acid, such as, for example, hydrochloric acid, trifluoroacetic acid or hydrobromic acid in glacial acetic acid, or in the presence of a base. Preferred bases are aqueous solutions of sodium hydroxide or potassium hydroxide.

The reaction temperatures can be varied within a substantial range in carrying out process (b) according to the invention. In general, the reaction is carried out at temperatures between $-20°$ C. and $+150°$ C., preferably at temperatures between $0°$ C. and $+120°$ C.

For carrying out process (b) according to the invention, in general 1 to 30 moles, preferably 1 to 15 moles, of acid or base are employed per mole of 5-acylaminopyrazole of the formula (Ia). The reaction is carried out and the reaction products of the formula (I) are worked up and isolated in the generally customary manner.

Possible diluents for carrying out process (c) according to the invention are likewise inert organic solvents. Ethers, such as, for example, tetrahydrofuran, or alcohols, such as methanol or ethanol, are preferably used.

Possible reducing agents for carrying out process (c) according to the invention are complex hydrides. Alkali metal borohydrides, such as lithium borohydride, sodium borohydride or sodium cyanoborohydride, are used in particular.

The reaction temperatures can be varied within a substantial range in carrying out process (c) according to the invention. In general, the reaction is carried out at temperatures between $-20°$ C. and $+150°$ C., preferably at temperatures between $0°$ C. and $+120°$ C.

For carrying out process (c) according to the invention, in general 1 to 5 moles, preferably 1 to 2 moles, of complex hydride are employed per mole of azomethine of the formula (IV). The reaction is carried out and the reaction products of the formula (I) are worked up and isolated in the generally customary manner.

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera

Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera

Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera

Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera

Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds of the formula (I) which can be used according to the invention also exhibit, besides a particularly good general herbicidal activity, a clearly improved crop plant selectivity in important crops, and can be used as selective agents for combating weeds both in dicotyledon crops, such as, for example, cotton plantations, and in monocotyledon crops, in particular cereals, such as, for example, wheat or oats. The azomethines of the formula (IV) used as intermediates also exhibit a herbicidal activity, and in particular also a selective herbicidal activity.

The active compounds can be converted to the customary formulations, such as solutions, emulsions, wettable powders, suspensions, powders dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example petroleum fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention, as such or in the form of their formulations, can also be used, for combating weeds, as mixtures with known herbicides, finished formulations or tank mixes being possible.

Possible components for the mixtures are known herbicides, such as, for example, 1-amino-6-ethylthio-3-(2,2-dimethylpropyl)-1,3,5-triazine-2,4(1H,3H)-dione or N-(2-benzothiazolyl)-N,N'-dimethylurea, for combating weeds in cereals; 4-amino-3-methyl-6-phenyl-1,2,4-triazin-5(4H)-one, for combating weeds in sugar beet, and 4-amino-6-(1,1-dimethylethyl)-3-methylthio-1,2,4-triazin-5(4H)-one, for combating weeds in soy beans. Mixtures with N,N-dimethyl-N'-(3-trifluoromethylphenyl)-urea, N,N-dimethyl-N'-(3-chloro-4-methylphenyl)-urea, N,N-dimethyl-N'-(4-isopropylphenyl)-urea, 4-amino-6-t-butyl-3-ethylthio-1,2,4-triazin-5(4)-one, 2,4-dichlorophenoxyacetic acid, 2,4-dichlorophenoxypropionic acid, (2-methyl-4-chlorophenoxy)-acetic acid, (4-chloro-2-methylphenoxy)-propionic acid, chloroacetic acid N-(methoxymethyl)-2,6-diethylanilide, 2-ethyl-6-methyl-N-(1-methyl-2-methoxyethyl)-chloroacetanilide, 2,6-dinitro-4-trifluoromethyl-N,N-dipropylaniline and methyl 5-(2,4-dichlorophenoxy)-2-nitrobenzoate; 3,5-diiodo-4-hydroxy-benzonitrile; 3-isopropyl-2,1,3-benzothiadiazin-4-one 2,2-dioxide; 2-chloro-N-{[(4-methoxy-6-methyl-1,3,5-triazin-2-yl)-amino]-carbonyl}-benzenesulphonamide; 4-ethylamino-2-t-butylamino-6-methylthio-S-triazine or N-(1-ethylpropyl)-3,4-dimethyl-2,6-dinitroaniline are also possible. Surprisingly, some mixtures also show a synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

The preparation and use of the active compounds according to the invention can be seen from the following examples.

PREPARATION EXAMPLES

Example 1

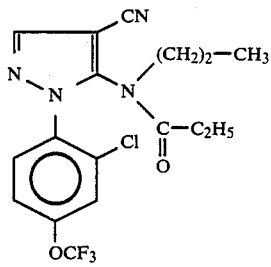

(Process a)

0.8 g (0.033 mole) of sodium hydride is added to 10.8 g (0.03 mole) of 4-cyano-5-propionylamino-1-(2-chloro-4-trifluoromethoxyphenyl)-pyrazole in 100 ml of tetrahydrofuran and, when the evolution of gas has ended, 10.2 g (0.06 mole) of n-propyl iodide are added and the mixture is stirred at the reflux temperature for 48 hours. For working up, the mixture is concentrated in vacuo, the residue is taken up in 200 ml of methylene chloride and the mixture is washed twice with 100 ml of water each time, dried over sodium sulphate and concentrated in vacuo. The oil which remains is purified by column chromatography (eluant: chloroform/acetone 9:1) and crystallised from petroleum ether. 8.0 g (66.6% of theory) of 4-cyano-1-(2-chloro-4-trifluoromethoxyphenyl)-5-(N-n-propyl-N-propionylamino)-pyrazole of melting point 83° C. are obtained.

Preparation of the starting compound

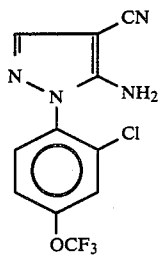

3.08 g (0.25 mole) of ethoxymethylenemalonic acid dinitrile and 5.7 g (0.025 mole) of 2-chloro-4-trifluoromethoxy-phenylhydrazine in 50 ml of ethylene glycol monoethyl ether are heated under reflux for 3 hours. After cooling, the reaction mixture is poured onto water and the crystalline precipitate is then filtered off with suction, stirred with petroleum ether, cooled and filtered off with suction again.

5.3 g (73.6% of theory) of 5-amino-4-cyano-1-(2-chloro-4-trifluoromethoxyphenyl)-pyrazole of melting point 115° C. are obtained.

Example 2

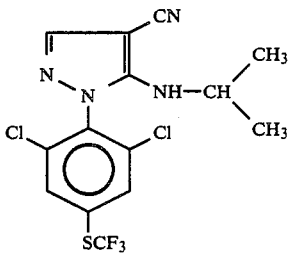

1.4 g (0.062 mole) of sodium hydride are added to 7.0 g (0.02 mole) of 4-cyano-5-amino-1-(2,6-dichloro-4-trifluoromethylthiophenyl)-pyrazole in 150 ml of tetrahydrofuran and, when the evolution of gas has ended, 17 g (0.1 mole) of i-propyl iodide are added and the mixture is stirred at room temperature. For working up, the mixture is concentrated in vacuo, the residue is taken up in 200 ml of methylene chloride and the mixture is washed twice with 100 ml of water each time, dried over sodium sulphate and concentrated in vacuo. The residue which remains in purified by column chromatography (eluant: chloroform/acetone=9:1).

5.2 g (66% of theory) of 4-cyano-1-(2,6-dichloro-4-trifluoromethylthio-phenyl)-5-isopropylamino-pyrazole of melting point 130° C. are obtained.

Example 3

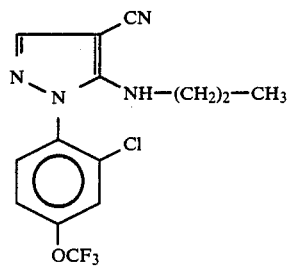

(Process b)

5.0 g (0.012 mole) of 1-(2-chloro-4-trifluoromethoxyphenyl)-4-cyano-5-(N-propionyl-N-n-propylamino)-pyrazole in 200 ml of methanol are stirred with 11.6 ml (0.012 mole) of 1 normal sodium hydroxide solution at room temperature for 48 hours. For working up, the mixture is concentrated in vacuo, the residue is taken up in methylene chloride, the mixture is washed twice with 100 ml of water each time, dried iover sodium sulphate and concentrated and the residue is crystallized from petroleum ether. 3.8 g (92% of theory) of 1-(2-chloro-4-trifluoromethoxyphenyl)-4-cyano-5-n-propylamino-pyrazole of melting point 63° C. are obtained.

The following compounds of the general formula (I) are obtained in a corresponding manner and in accordance with the general preparation examples:

TABLE 2

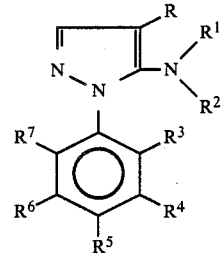

(I)

| Example No. | R | $R^1$ | $R^2$ | $R^3$ | $R^4$ | $R^5$ | $R^6$ | $R^7$ | melting point (°C.) |
|---|---|---|---|---|---|---|---|---|---|
| 4 | CN | $CH_3$ | $CH_3OCO-$ | Cl | H | $-OCF_3$ | H | H | Oil |
| 5 | CN | $CH_3$ | H | Cl | H | $-OCF_3$ | H | H | 165–166 |
| 6 | CN | $C_2H_5$ | $C_2H_5CO-$ | Cl | H | $-OCF_3$ | H | H | 68 |
| 7 | CN | $CH_3$ | $CH_3OCO-$ | Cl | H | $-OCF_3$ | H | Cl | Oil |
| 8 | CN | $C_2H_5$ | H | Cl | H | $-OCF_3$ | H | H | 78 |
| 9 | CN | $CH_3$ | $C_2H_5CO-$ | Cl | H | $-SO_2CF_3$ | H | Cl | 164 |
| 10 | CN | $CH_3$ | $C_2H_5CO-$ | Cl | H | $-OCF_3$ | H | Cl | 108 |
| 11 | CN | $CH_3$ | H | Cl | H | $-OCF_3$ | H | Cl | 157–158 |
| 12 | CN | $CH_3$ | $C_2H_5CO-$ | Cl | H | $-SCF_3$ | H | Cl | 108 |
| 13 | CN | $CH_3$ | H | Cl | H | $-SCF_3$ | H | Cl | 177 |
| 14 | CN | $CH_3$ | H | Cl | H | $-SO_2CF_3$ | H | Cl | 52 |
| 15 | CN | $C_3H_7$ | H | Cl | H | $-SCF_3$ | H | Cl | Oil |
| 16 | CN | $C_3H_7$ | $C_3H_7$ | Cl | H | $-SCF_3$ | H | Cl | Oil |

TABLE 2-continued

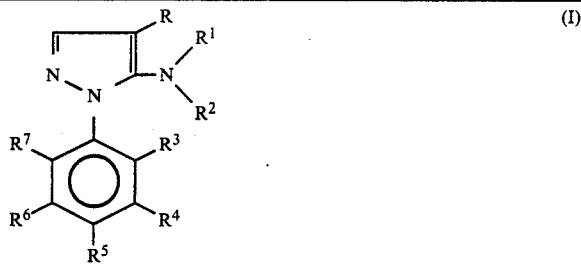

| Example No. | R | R¹ | R² | R³ | R⁴ | R⁵ | R⁶ | R⁷ | melting point (°C.) |
|---|---|---|---|---|---|---|---|---|---|
| 17 | CN | iC₃H₇ | H | Cl | H | —OCF₃ | H | H | 90 |
| 18 | CN | iC₃H₇ | H | Cl | H | —OCF₃ | H | Cl | 138 |
| 19 | CN | C₂H₅ | H | Cl | H | —OCF₃ | H | Cl | 112 |
| 20 | CN | C₂H₅ | H | Cl | H | —SCF₃ | H | Cl | 114 |
| 21 | CN | C₂H₅OCOCH₂— | CH₃CO— | Cl | H | —SCF₃ | H | Cl | 126 |
| 22 | CN | CH₃OCOCH—<br>\|<br>CH₃ | H | Cl | H | —OCF₃ | H | H | 85–89 |

Use Examples

The compounds listed below are employed as comparison substances in the use examples which follow:

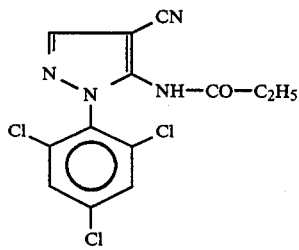

(A)

4-Cyano-5-propionylamino-1-(2,4,6-trichlorophenyl)-pyrazole (known from DE-OS (German Published Specification) No. 3,226,513);

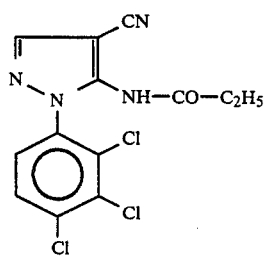

(B)

4-Cyano-5-propionylamino-1-(2,3,4-trichlorophenyl)-pyrazole (known from DE-OS (German Published Specification) No. 3,226,513).

EXAMPLE

Pre-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0%=no action (like untreated control)
100%=total destruction

In this example, the compound according to preparation Example (5), for example, exhibits a clear superiority in selectivity towards useful plants in comparison with the prior art; this applies particularly to wheat and cotton.

EXAMPLE

Post-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0%=no action (like untreated control)
100%=total destruction

In this example, the compound according to preparation Example (3), for example, exhibits a clear superiority in herbicidal action, as well as in selectivity towards useful plants, in comparison with the prior art. This applies particularly to oats.

It will be understood that the specification and examples are illustrative but not limitative of the present invention and that other embodiments within the spirit and scope of the invention will suggest themselves to those skilled in the art.

We claim:

1. A substituted 5-amino-1-phenylpyrazole of the formula

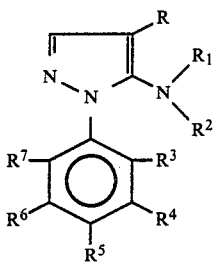

in which
R represents cyano or aminocarbonyl, or represents alkoxycarbonyl, alkenyloxycarbonyl, alkinyloxycarbonyl, alkylaminocarbonyl, alkenylaminocarbonyl, alkinylaminocarbonyl, dialkylaminocarbonyl, dialkenylaminocarbonyl or dialkinylaminocarbonyl, each of which has up to 5 carbon atoms in the individual aliphatic radicals and each of which is straight-chain or branched, $R^1$ represents alkyl, alkenyl or alkinyl, each of which has up to 8 carbon atoms and each of which is optionally substituted by at least one member selected from the group consisting of halogen, cyano, nitro, hydroxyl and carboxyl, alkoxy and alkoxycarbonyl, each of which has up to 6 carbon atoms and each of which is straight-chain or branched, and aminocarbonyl which is optionally substituted by methyl, ethyl, propyl, allyl, propargyl methoxy, methylsulphonyl or ethylsulphonyl, it being possible for the nitrogen atom of the aminocarbonyl radical also to be part of a pyrrolidine, piperidine, morpholine or perhydroazepine radical; or represents cycloalkyl which has 3 to 7 carbon atoms and is optionally substituted by at least one radical selected from the group consisting of halogen and straight-chain or branched alkyl with 1 to 4 carbon atoms, $R^2$ independently of $R^1$ represents the same radicals as $R^1$, and also may represent hydrogen or a radial

X represents oxygen or sulphur and
$R^8$ represents hydrogen, or represents alkyl, alkenyl, alkinyl, alkoxyalkyl, alkylthioalkyl, alkoxy, alkylthio, alkylamino, dialkylamino or halogenoalkyl, each of which has up to 4 carbon atoms in the individual alkyl, alkenyl or alkinyl parts and each of which is straight-chain or branched, halogenoalkyl having up to 9 identical or different halogen atoms, or represents cycloalkyl which has 3 to 7 carbon atoms and is optionally substituted by at least one member selected from the group consisting of halogen, lower alkyl and lower halogenoalkyl, or represents phenyl, phenoxy, phenylthio or phenylamino, each of which is optionally substituted by at least one member selected from the group consisting of halogen and alkyl, alkoxy and halogenoalkyl, each of which has up to 4 carbon atoms and each of which is straight-chain or branched, halogenoalkyl having up to 9 identical or different halogen atoms, and $R^3$, $R^4$, $R^5$, $R^6$ and $R^7$ independently of one another represent hydrogen, fluorine, chlorine, bromine, iodine or nitro, or alkyl, alkoxy, alkylsulphonyl or alkoxycarbonyl, each of which has up to 4 carbon atoms in the particular alkyl parts and each of which is straight-chain or branched, or represent a radical $-X'-R^9$, wherein
$X'$ represents oxygen, sulphur, sulphinyl or sulphonyl, and
$R^9$ represents straight-chain or branched halogenoalkyl with up to 4 carbon atoms and up to 9 identical or different halogen atoms, with the proviso that at least one of the radicals $R^3$, $R^4$, $R^5$, $R^6$ or $R^7$ represents a radical $-X'-R^9$, but R does not represent cyano at the same time as $R^5$ represents trifluoromethyl.

2. A substituted 5-amino-1-phenylpyrazole according to claim 1,
in which
R represents cyano, methoxycarbonyl, ethoxycarbonyl, allyloxycarbonyl, propargyloxycarbonyl, aminocarbonyl, methylaminocarbonyl, dimethylaminocarbonyl, ethylaminocarbonyl, diethylaminocarbonyl, diallylaminocarbonyl or dipropargylaminocarbonyl, $R^1$ represents methyl, ethyl, n- or i-propyl, n-, i-, s- or t-butyl, allyl, butenyl, propargyl or butinyl, each of which is optionally mono-, di- or trisubstituted by at least one substituent selected from the group consisting of fluorine, chlorine, bromine, iodine, cyano, nitro, hydroxyl, carboxyl, methoxy, ethoxy, n- or i-propoxy, methoxycarbonyl, ethoxycarbonyl, n- or i-propoxycarbonyl, n-, i-, s- or t-butoxycarbonyl, aminocarbonyl, N-methylaminocarbonyl, N-ethylaminocarbonyl, N,N-dimethylaminocarbonyl, N,N-diethylaminocarbonyl, N,N-diallylaminocarbonyl, N-methyl-N-ethylaminocarbonyl, N-methyl-N-propylaminocarbonyl, N-methyl-N-allylaminocarbonyl, N-methyl-N-propargylaminocarbonyl, N-methyl-N-methoxyaminocarbonyl, N-methylsulphonylaminocarbonyl, N-ethylsulphonylaminocarbonyl, pyrrolidin-1-ylcarbonyl, piperidin-1-ylcarbonyl, morpholin-4-ylcarbonyl and perhydroazepin-1-ylcarbonyl; or represents cyclopropyl, cyclopentyl, cyclohexyl or cycloheptyl, each of which is optionally mono-, di-, tri-, tetra- or pentasubstituted by identical or different substituents from the group consisting of chlorine, methyl and ethyl, $R^2$ independently of $R^1$ represents the same radicals as $R^1$, and additionally may represent hydrogen or a radical

wherein

X represents oxygen or sulphur and

R⁸ represents hydrogen, methyl, ethyl, n- or i-propyl, allyl, propargyl, butenyl, methoxymethyl, ethoxymethyl, methoxyethyl, ethoxyethyl, methylthiomethyl, methoxy, ethoxy, methylthio, ethylthio, methylamino, ethylamino, dimethylamino, trifluoromethyl, trichloroethyl, dichlorofluoroethyl, difluorochloroethyl, chloromethyl, iodomethyl, bromomethyl, dichloromethyl, 1-chloroethyl, 2-chloroethyl, 2-bromoethyl or heptafluoro-n-propyl, or represents cyclopropyl, cyclopentyl or cyclohexyl, each of which is optionally mono-, di-, tri- or tetra-substituted by at least one substituent selected from the group consisting of fluorine, chlorine, bromine, methyl and trifluoromethyl, or represents phenyl, phenoxy, phenylthio or phenylamino, each of which is optionally mono-, di- or tri-substituted by at least one substituent selected from the group consisting of methyl, methoxy, chlorine and trifluoromethyl, and $R^3$, $R^4$, $R^5$, $R^6$ and $R^7$ independently of one another represent hydrogen, fluorine, chlorine, broine, cyano, nitro, methyl, ethyl, n- or i-propyl, methoxy, ethoxy, methylsulphonyl, methoxycarbonyl or ethoxycarbonyl, or represent a radical —(X')$_n$—R⁹, wherein X' represents oxygen, sulphur, sulphinyl or sulphonyl, n represents 0 or 1 and R⁹ represents trifluoromethyl, trichloromethyl, dichlorofluoromethyl, difluorochloromethyl, dichloromethyl, chloromethyl, difluoromethyl, pentafluoroethyl, tetrafluoroethyl, trifluorochloroethyl, trifluoroethyl, difluorodichloroethyl, trifluorodichloroethyl or pentachloroethyl, with the proviso that at least one of the radicals $R^3$, $R^4$, $R^5$, $R^6$ or $R^7$ represents a radical —(X')$_n$—R⁹, but R does not represent cyano at the same time as $R^5$ represents trifluoromethyl.

3. A compound according to claim 1, wherein such compound is 4-cyano-1-(2-chloro-4-trifluoromethoxyphenyl)-5-methylamino-pyrazole of the formula

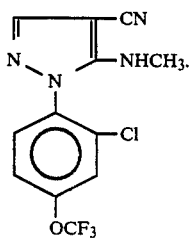

4. A compound according to claim 1, wherein such compound is 4-cyano-1-(2,6-dichloro-4-trifluoromethoxyphenyl)-5-(N-methyl-N-methoxycarbonylamino)-pyrazole of the formula

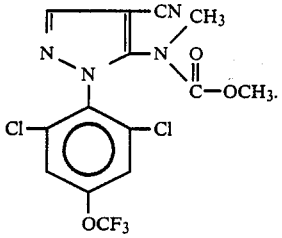

5. A compound according to claim 1, wherein such compound is 4-cyano-1-(2,6-dichloro-4-trifluoromethoxyphenyl)-5-methylamino-pyrazole of the formula

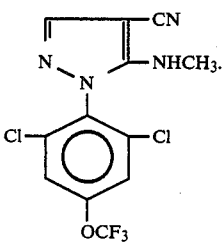

6. A compound according to claim 1, wherein such compound is 4-cyano-1-(2-chloro-4-trifluoromethoxyphenyl)-5-isopropylamino-pyrazole of the formula

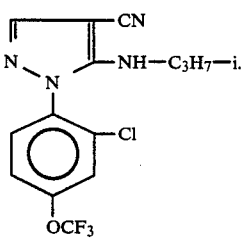

7. A compound according to claim 1, wherein such compound is 4-cyano-1-(2,6-dichloro-4-trifluoromethoxyphenyl)-5-isopropylamino-pyrazole of the formula

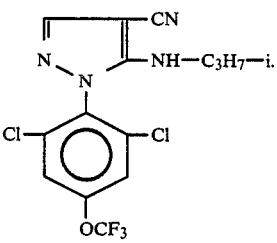

8. A substituted 5-amino-1-phenylpyrazole according to claim 1, in which

R represents cyano,

R¹ represents alkyl with up to 8 carbon atoms and optionally substituted by alkoxycarbonyl with up to 6 carbon atoms, R² represents hydrogen, $R^3$, $R^4$, $R^6$ and $R^7$ independently of one another represent hydrogen, fluorine, chlorine, bromine or iodine, and $R^5$ represents trifluoromethoxy, trifluoromethylthio or trifluoromethylsulphonyl.

9. A herbicidal composition comprising a herbicidally effective amount of a compound according to claim 1 in admixture with a diluent.

10. A method of combating unwanted vegetation which comprises applying to such vegetation or to a locus from which it is desired to exclude such vegetation a herbicidally effective amount of a compound according to claim 1.

11. The method according to claim 10, wherein such compound is
4-cyano-1-(2-chloro-4-trifluoromethoxyphenyl)-5-methylamino-pyrazole,
4-cyano-1-(2,6-dichloro-4-trifluoromethoxyphenyl)-5-(N-methyl-N-methoxycarbonylamino)-pyrazole,
4-cyano-1-(2,6-dichloro-4-trifluoromethoxyphenyl)-5-methylamino-pyrazole,
4-cyano-1-(2-chloro-4-trifluoromethoxyphenyl)-5-isopropylamino-pyrazole, or
4-cyano-1-(2,6-dichloro-4-trifluoromethoxyphenyl)-5-isopropylamino-pyrazole.

* * * * *